United States Patent [19]

Pelosi, Jr. et al.

[11] Patent Number: 4,643,996
[45] Date of Patent: Feb. 17, 1987

[54] 5-PHENYL-2-FUROIC ACID HYDRAZIDES

[75] Inventors: Stanford S. Pelosi, Jr.; Chia-Nien Yu, both of Norwich, N.Y.

[73] Assignee: Norwich Eaton Pharmaceuticals, Inc., Norwich, N.Y.

[21] Appl. No.: 389,627

[22] Filed: Jun. 18, 1982

[51] Int. Cl.$^4$ .................. A61K 31/34; A61K 31/44; C07D 307/52; C07D 307/54

[52] U.S. Cl. .................. 514/336; 514/471; 546/283; 549/487

[58] Field of Search .................. 549/487; 542/418; 424/263, 285; 514/336, 471; 546/283

[56] References Cited

U.S. PATENT DOCUMENTS 4,162,257 7/1979 Pelosi et al. .................. 549/487
4,199,508 4/1980 Yu .................. 548/143

OTHER PUBLICATIONS

Oleinik et al, Klim. Farm. Zh., 10:46 (1976).

Primary Examiner—Richard Raymond
Attorney, Agent, or Firm—Milton B. Graff, IV; Jack D. Schaeffer; Richard C. Witte

[57] ABSTRACT

Certain 5-phenyl-2-furoic acid hydrazides of the formula:

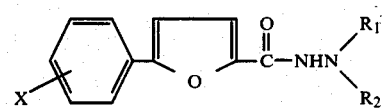

wherein X represents 4-chloro, 4-fluoro, 3-trifluoromethyl or hydrogen, $R_1$ represents hydrogen or methyl, $R_2$ represents acetyl, isopropyl or methyl, and $R_1$ and $R_2$ taken together represent isopropylidene or 4-pyridinylmethylene are useful as anti-inflammatory agents.

3 Claims, No Drawings

5-PHENYL-2-FUROIC ACID HYDRAZIDES

This invention is concerned with chemical compounds and particularly with 5-phenyl-2-furoic acid hydrazides of the formula:

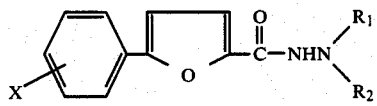

wherein X represents 4-chloro, 4-fluoro, 3-trifluoromethyl or hydrogen, $R_1$ represents hydrogen or methyl, $R_2$ represents acetyl, isopropyl or methyl, and $R_1$ and $R_2$ taken together represent isopropylidene or 4-pyridinylmethylene and a method for their preparation.

Some of these compounds wherein X represents hydrogen or 4-chloro and $R_1$ and $R_2$ represent hydrogen and their preparations have been described in the chemical literature to possess tuberculostatic activity [Oleinik et al., Khim. Farm. Zh. 10:46(1976)]. It has now been discovered that these compounds and the compounds with X, $R_1$ and $R_2$ previously ascribed possess anti-inflammatory activity as evidenced by their ability to inhibit edema induced by the administration of carrageenin. Thus, when they are administered orally at a dose of 300 mg/kg suspended in a vehicle such as aqueous methyl cellulose per os to rats receiving carrageenin, edema resulting from that substance is inhibited by 40-85% at 4 hours and 43-92% at 6 hours [Winter et al., P.S.E.B.M. 111:544(1962)].

The compounds of this invention can be combined in various pharmaceutical dosage forms such as capsules, tablets, dragees, suspensions and the like using excipients and adjuvants commonplace in the pharmaceutical art and with which there is no incompatibility.

The compounds of this invention are readily prepared. The compounds wherein X represents hydrogen, 4-chloro, 4-fluoro, or 3-trifluoromethyl and $R_1$ and $R_2$ represent hydrogen were prepared according to the method described in the chemical literature [Oleinik et al., Khim. Farm. Zh. 10:46(1976)]. In order that this invention may be readily available to and understood by those skilled in the art, the following examples are supplied for the preparation of the remaining compounds wherein X, $R_1$, and $R_2$ have been previously ascribed.

EXAMPLE I 5-(p-Chlorophenyl)-2-furoic Acid 1-Acetylhydrazine

A mixture of 111.5 g (0.50 mole) of 5-(p-chlorophenyl)-2-furoic acid in 500 ml of thionyl chloride was heated at refluxed for 1¾ hr. After slight cooling, the reaction mixture was filtered and the filtrate was concentrated in a water bath at reduced pressure to a creamy solid. The solid was dissolved in 400 ml of chloroform. To this chloroform solution under stirring at room temperature was added a suspension of 74 g (1.0 mole) of acetylhydrazine in 900 ml of chloroform. Addition was completed in about 20 min. White creamy solid separated fairly readily while the temperature rose to about 45°. The mixture was allowed to stir at ambient temperature overnight. The mixture was filtered and the solid was washed with chloroform and air dried. The solid was further triturated with water, filtered, washed with water again and air dried. The yield of crude product was 120 g (89%). Recrystallization from ethyl acetate gave 95 g of product, m.p. 206°-208°.

Anal. Calcd. for $C_{13}H_{11}ClN_2O_3$: C, 56.02; H, 3.98; N, 10.05. Found: C, 55.95; H, 3.99; N, 9.99.

EXAMPLE II 5-(p-Chlorophenyl)-2-furoic Acid 2,2-Dimethylhydrazide

To a solution of 36 g (0.60 mole) of dimethylhydrazine and 150 ml of benzene was added portionwise 60 g (0.25 mole) of 5-(p-chlorophenyl)-2-furoyl chloride with the temperature being controlled below 50° by means of an ice bath. The reaction mixture was refluxed for 2 hours with dissolution, cooled and the resulting precipitate filtered, washed with water and dried at 60° to yield 48 g (73%). An analytical sample was prepared by recrystallizing a sample from ethyl acetate/Darco and drying in the vacuum pistol at room temperature, m.p. 150°-152°.

Anal. Calcd. for $C_{13}H_{13}ClN_2O_2$: C, 58.98; H, 4.95; N, 10.58. Found: C, 58.70; H, 5.05; N, 10.33.

EXAMPLE III 5-(p-Chlorophenyl)-2-furoic Acid Isopropylidenehydrazide

A mixture of 50 g (0.21 mole) of 5-(p-chlorophenyl)-2-furoic acid hydrazide in 500 ml of acetone was heated at reflux overnight. The reaction mixture was filtered while still warm. Crystalline solid separated readily from the filtrate upon cooling. The solid was collected, washed well with acetone and air dried. The yield was 40 g (69%). Recrystallization of 2 g from acetone gave 1.3 g of analytically pure product, m.p. 167°-169°.

Anal. Calcd. for $C_{14}H_{13}ClN_2O_2$: C, 60.76; H, 4.74; N, 10.13. Found: C, 60.79; H, 4.71; N, 10.07.

EXAMPLE IV 5-(p-Chlorophenyl)-2-furoic Acid 1-Isopropylhydrazide

To a yellow solution of 28.3 g (0.12 mole) of the compound of Example III in 500 ml of anhydrous methanol (dissolved with slight warming) was added 3.9 g (0.12 mole) of sodium borohydride in small portions such that the temperature was maintained below 35°. Addition was completed in about 40 min. The reaction mixture was allowed to stir at ambient temperature for 1 hr and then was heated at reflux for ½ hr. The yellow reaction solution was filtered and the filtrate was concentrated under reduced pressure to a yellow pasty solid. The solid was partitioned between chloroform and water. The chloroform layer was dried over MgSO₄. After filtering off MgSO₄, the filtrate was concentrated under reduced pressure to a pale yellow solid residue. The solid was recrystallized from 1800 ml of cyclohexane to give 22 g (66%) of white crystalline product, m.p. 142°-144°.

Anal. Calcd. for $C_{14}H_{15}ClN_2O_2$: C, 60.32; H, 5.42; N, 10.05. Found: C, 60.23; H, 5.30; N, 9.95.

EXAMPLE V 5-(p-Chlorophenyl)-2-furoic Acid Isonicotinylidenehydrazide

To a stirring mixture of 59 g (0.25 mole) of 5-(p-chlorophenyl)-2-furoic acid hydrazide in 350 ml of anhydrous methanol was added portionwise 27 g (0.25 mole) of 4-pyridinecarboxaldehyde with the temperature rising to 30° and dissolution. After stirring at ambient temperature for ca. 10 min. a mixture formed which was then refluxed overnight. The solid was filtered and recrystallized from nitromethane/Darco to yield 67 g (82%). An analytical sample was prepared by recrystallizing a sample a second time from nitromethane, m.p. 204°–206°.

Anal. Calcd. for $C_{17}H_{12}ClN_3O_2$: C, 62.67; H, 3.71; N, 12.90. Found: C, 62.31; H, 4.09; N, 12.82.

What is claimed is:

1. The compound 5-(p-chlorophenyl)-2-furoic acid isopropylidenehydrazide.

2. The compound 5-(p-chlorophenyl)-2-furoic acid isonicotinylidenehydrazide.

3. A method of treating inflammation which comprises orally administering to a host in need thereof an anti-inflammatory amount of a compound of the formula:

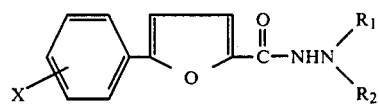

wherein X represents 4-chloro, 4-fluoro, 3-trifluoromethyl or hydrogen, $R_1$ represents hydrogen or methyl, $R_2$ represents acetyl, isopropyl or methyl, and $R_1$ and $R_2$ taken together represent isopropylidene or 4-pyridinylmethylene in acceptable pharmaceutical dosage form.

* * * * *